US006495714B1

(12) United States Patent
Halbritter et al.

(10) Patent No.: US 6,495,714 B1
(45) Date of Patent: Dec. 17, 2002

(54) METHOD FOR PRODUCING ALKANESULFONIC ACIDS

(75) Inventors: Klaus Halbritter, Heidelberg (DE); Hans-Josef Sterzel, Dannstadt-Schauernheim (DE); Matthias Eiermann, Limburgerhof (DE); Eva Freudenthaler, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/890,767

(22) PCT Filed: Feb. 3, 2000

(86) PCT No.: PCT/EP00/00860

§ 371 (c)(1),
(2), (4) Date: Aug. 3, 2001

(87) PCT Pub. No.: WO00/46188

PCT Pub. Date: Aug. 10, 2000

(30) Foreign Application Priority Data

Feb. 3, 1999 (DE) .......................................... 199 04 262

(51) Int. Cl.[7] .............................................. C07C 309/00
(52) U.S. Cl. ...................... 562/117; 562/117; 562/115; 562/118
(58) Field of Search ................................. 562/117, 115, 562/118

(56) References Cited

U.S. PATENT DOCUMENTS 2,697,722 A   12/1954   Johnson et al.
2,727,920 A   12/1955   Johnson et al.

OTHER PUBLICATIONS

Razuvaev et al (Zhur. Obshchei Khim, 1961, 31, 1328–32).*
Davis et al (J. Amer. Chem. Soc. 1962, vol. 84, No. 4, pp. 599–604).*
Bissinger et al (J. Amer. Chem. Soc. 1948, vol. 70, No. 11, pp. 3940–3941).*
March (Advanced Organic Chemistry, Jerry March, 3rd edition, 1985, p. 444).*
W. E. Bissinger, et al., Journal of the American Chemical Society, vol. 70, No. 11, pp. 3940–3941, "Rearrangement of Alkyl Sulfites to Alkanesulphonate Esters," Dec. 8, 1948.
A. Simon, et al., Chemische Berichte, vol. 89, No. 4, pp. 883–894, "Ueber Die Methylierung Des Sulfitions and Ueber Die Umlagerungsmechanismen Der Schwefligsaeure–in Sulfonsaeure–Abkoemmlinge," 1956.
A. J. W. Brook, et al., Physical Organic Chemistry, No. 6, pp. 1161–1163, "The Mechanism of the Isomerisation of Dimethyl Sulphite to Methyl Methanesulphonate," 1971.
R. E. Davis, Journal of the American Chemical Society, vol. 84, No. 4, pp. 599–604, "Hydrolysis of Ethylene and Dimethyl Sulfite and The Origin of Strain in Cyclic Esters," Feb. 20, 1962.
A. V. Devekki, et al., Journal of Organic Chemistry of the USSR, vol. 19, No. 5, pp. 829–834, "Coordination and Catalytic Reactions of Unsaturated Compounds," May 1983.

* cited by examiner

Primary Examiner—Johann Richter
Assistant Examiner—Farhad Forohar
(74) Attorney, Agent, or Firm—Oblon, Spivak, McClelland, Maier & Neustadt, P.C.

(57) ABSTRACT

A process for preparing alkanesulfonic acids from dialkyl sulfites comprises the following steps:
  rearrangement of dialkyl sulfite in the presence of a suitable catalyst to form the corresponding alkyl alkanesulfonate and
  hydrolysis of the resulting alkyl alkanesulfonate to give the corresponding alkanesulfonic acid.

21 Claims, No Drawings

METHOD FOR PRODUCING ALKANESULFONIC ACIDS

This Application is a 371 of PCT/EP00/00860 filed on Feb. 3, 2000.

The invention relates to a process for preparing alkanesulfonic acids.

Alkanesulfonic acids are used in a number of industrial applications. Long-chain alkanesulfonic acids have, for example, surfactant properties, while short-chain acids such as methanesulfonic acid can be used, for example, as auxiliaries in the electrolytic deposition of base metals such as tin or lead in the tin plating of circuit boards for electronics or in the production of tin plate.

The literature describes a number of processes for preparing alkanesulfonic acids. In these, particularly in the case of lower alkanesulfonic acids, starting materials employed are alkyl mercaptans or dialkyl disulfides which are usually prepared by reacting hydrogen sulfide with alcohols. The oxidation of the alkyl mercaptans or dialkyl disulfides to the corresponding alkanesulfonic acids can be achieved by means of various oxidizing agents. Thus, it is possible to use hydrogen peroxide, chlorine, dimethyl sulfoxide and hydroiodic acid as oxidizing agent or to employ electrochemical oxidation.

A further way of preparing alkanesulfonic acids is the oxidation of alkyl mercaptans or dialkyl disulfides by oxygen in the presence of oxides of nitrogen or of nitric acid. The oxidation using oxygen in the presence of nitric acid is described, for example, in U.S. Pat. Nos. 2,697,722 and 2,727,920.

These processes have the disadvantage that they start out from the extremely toxic or unpleasant-smelling substances hydrogen sulfide, alkyl mercaptan and/or dialkyl disulfide. Even in very small concentrations far below the MAC (maximum workplace concentration), these have an extremely strong odor and their handling therefore requires a considerable outlay in terms of safety measures.

It is an object of the present invention to provide a process for preparing alkanesulfonic acids which avoids the use of these toxic and unpleasant-smelling substances and can thus be carried out with less outlay in terms of safety. We have found that this object is achieved by a process for preparing alkanesulfonic acids from dialkyl sulfites, which comprises the following steps:

rearrangement of dialkyl sulfite in the presence of a suitable catalyst to form the corresponding alkyl alkanesulfonate and hydrolysis of the resulting alkyl alkanesulfonate to give the corresponding alkanesulfonic acid.

Rearrangement of Dialkyl Sulfite to Form the Corresponding Alkyl Alkanesulfonate The rearrangement of the dialkyl sulfite to form the alkyl alkanesulfonate is carried out in the presence of a suitable catalyst. Useful catalysts are, for example, bases such as amines, preferably tertiary amines, e.g. dimethylaniline or tri-n-butylamine, or heterocyclic amines such as piperidine or pyridine. Alkyl iodide and quaternary ammonium salts, quaternary phosphonium salts or tertiary sulfonium salts and also alkylating agents are also suitable. Preference is given to using tri-n-butylamine as catalyst.

The catalyst is generally used in an amount of from 0.01 to 20 mol %, preferably from 0.1 to 10 mol %, particularly preferably from 1 to 5 mol %.

The rearrangement is usually carried out at from 20 to 250° C., preferably from 50 to 200° C., particularly preferably from 120 to 180° C.

Such rearrangements are described in W. Voss et al., Justus Liebigs Ann. Chem. 485 (1931) 258–283; W. E. Bissinger et al., J. Am. Chem. Soc. 70 (1948) 3940; A. Simon et al., Chem. Ber. 89 (1956) 883; A. J. W. Brook et al., J. Chem. Soc. B (1971) 1061.

The reaction mixture obtained at the end of the reaction, which comprises the alkyl alkanesulfonate, is worked up if necessary, preferably by distillation, particularly preferably by vacuum distillation in order to avoid excessively high temperatures at the bottom and thus partial decomposition of the reaction product, which frequently takes place.

Distillation of the reaction mixture comprising the alkyl alkanesulfonate is advantageous since this may enable distillation of the alkanesulfonic acid prepared in the following step to be avoided. An acid distillation, such as that of the alkanesulfonic acid, generally has to be carried out in corrosion-resistant apparatuses at high temperatures, while the distillation of the corresponding ester can generally be carried out at lower temperatures and in a simpler distillation column made of material which is not corrosion resistant.

The reaction product of this step, namely the alkyl alkanesulfonate, can be obtained in yields of generally >60% (based on the dialkyl sulfite used).

Hydrolysis of the Alkyl Alkanesulfonate to Give the Alkanesulfonic Acid

The hydrolysis of the alkyl alkanesulfonate to give the corresponding alkanesulfonic acid can be carried out directly using water (W. Voss et al., Justus Liebigs Ann. Chem. 485 (1931) 265; P. M. Laughton et al., Can. J. Chem. 34 (1956) 1714–1718).

In general, the hydrolysis is carried out at elevated temperature without catalyst. For this purpose, water is added in an amount of generally from 50 to 500 mol %, preferably from 100 to 200 mol %, particularly preferably 120 mol %. The hydrolysis is generally carried out at from 80 to 180° C., preferably from 100 to 150° C., particularly preferably 120° C. The hydrolysis is preferably carried out in a continuously operated reactor having a superposed column via which the alcohol liberated is removed.

The hydrolysis forms the desired alkanesulfonic acid, usually in aqueous solution, and the alcohol corresponding to the alkyl alkanesulfonate used. The alcohol is distilled off. If a nonaqueous alkanesulfonic acid is required, the aqueous solution has to be worked up, e.g. by distillation.

Synthesis of Dialkyl Sulfite

The dialkyl sulfite used for the synthesis of the alkyl alkanesulfonate can be prepared in any desired way. Thus, for example, dimethyl sulfite can be prepared 1from thionyl chloride and methanol (W. Voss, DE-A 487253; A. J. Vogel et al., J. Chem. Soc. 16 (1943) 16; W. E. Bissinger et al., J. Am. Chem. Soc. 69 (1947) 2159). However, these reactions starting from thionyl chloride have the disadvantage that they form hydrogen chloride which, in terms of corrosion, places particular demands on the materials to be used.

In a preferred embodiment, the dialkyl sulfite is therefore obtained by reaction of alkylene sulfite with an alcohol. In this reaction, the diol corresponding to the alkylene sulfite is formed as by-product. As alcohol, it is usual to use a monohydric alcohol, i.e. an alcohol having one OH group. The alkyl radical of the alcohol used corresponds to that of the alkanesulfonic acid desired as end product.

As alkylene sulfite, it is possible to use alkylene sulfites of the formula I:

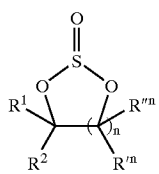

(I)

In the formula I, n is generally from 1 to 6, preferably from 1 to 4, particularly preferably 1 or 2, very particularly preferably 1. $R^1$, $R^2$, $R'''$ and $R''''$ are independently hydrogen, alkyl or aryl radicals. Particularly preferably, $R^1$, $R^2$, $R'''$ and $R''''$ are independently hydrogen or methyl radicals. Very particular preference is given to using ethylene sulfite and propylene sulfite.

The diol formed as by-product in this reaction, very particularly preferably ethylene glycol, has a variety of uses in industry, for example as a component for cooling fluids, as medium for heat transfer, as hydraulic fluid, as solvent or as starting material for further syntheses.

This reaction of the alkylene sulfite with an alcohol to give the desired dialkyl sulfite and the diol corresponding to the alkylene sulfite is an equilibrium reaction. In order to shift the equilibrium in the direction of dialkyl sulfite, continual removal of the diol formed is necessary.

A simple, continual distillation of the diol from the reaction mixture is generally not possible, since, particularly in the preparation of dimethyl sulfite, the alcohol used is usually the lowest-boiling component and would therefore distil off first. This would result in a shift in the equilibrium to the left, i.e. in the direction of the starting materials.

However, a generally quantitative reaction of the alkylene sulfite with an alcohol to give the desired dialkyl sulfite is possible in a column by a method described in the application DE-A 199 04 261 having the title "Process for preparing dimethyl sulfite", which was filed on the same day and is not a prior publication.

This process is a process for preparing dimethyl sulfite by reaction (transesterification) of a cyclic alkylene sulfite having at least two carbon atoms with methanol, in the presence or absence of a catalyst, with the process being carried out continuously in a column.

The process is preferably carried out in countercurrent, with methanol being added in the lower part of the column and flowing toward the cyclic alkylene sulfite added in the upper part of the column. The diol corresponding to the cyclic alkylene sulfite used is liberated in the reaction (transesterification) and is taken off continuously at the bottom of the column and the dimethyl sulfite formed, together with unreacted methanol, is taken off continuously at the top of the column. In this way, a generally complete conversion of the alkylene sulfite used is achieved.

The reaction of alkylene sulfite with an alcohol to form dialkyl sulfite and diol can, if desired, be carried out in the presence of a catalyst. Suitable catalysts are generally acidic or basic substances. Examples of suitable catalysts are described in R. E. Davis, J. Am. Chem. Soc. 84 (1992) 599–604; P. A. Bristow et al., Tetrahedron Letters 10 (1967) 901–903; P. A. Bristow et al., J. Chem. Soc. C (1968) 685–687. Preference is given to using methanesulfonic acid as catalyst. The catalyst is usually used in an amount of from 0.01 to 5 mol %, preferably from 0.1 to 1 mol %.

Synthesis of the Alkylene Sulfite

The synthesis of the alkylene sulfite used for preparing the dialkyl sulfite can be carried out in any desired way. Thus, for example, ethylene sulfite can be prepared by reacting thionyl chloride with ethylene glycol (JP-A 7033763). However, some alkylene sulfites, e.g. ethylene sulfite, are preferably prepared by reacting epoxides with sulfur dioxide, in the presence or absence of a catalyst.

As epoxides, it is possible to use epoxides of the formula II corresponding to the desired alkylene sulfites:

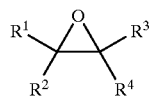

(II)

In the formula II, $R^1$, $R^2$, $R^3$ and $R^4$ are independently hydrogen, alkyl or aryl radicals; $R^1$, $R^2$, $R^3$ and $R^4$ are preferably, independently of one another, hydrogen or methyl radicals. Particular preference is given to using ethylene oxide and propylene oxide. Very particular preference is given to using ethylene oxide.

If desired, catalysts such as tetraethylammonium halides or amines can be added. The use of such catalysts is described in G. A. Razuvaev et al., ⋅ ob• . Chim. 31 (1961) 1328–1332 and GB-A 844 104.

The catalyst is generally added in an amount of from 0.01 to 10% by weight, preferably from 0.1 to 5% by weight, particularly preferably 1% by weight.

The present invention further provides for the preparation of alkanesulfonic acids, comprising the following steps:

(a) reaction of an epoxide with sulfur dioxide, in the presence or absence of a suitable catalyst, to form alkylene sulfite, (b) reaction of the alkylene sulfite with an alcohol, in the presence or absence of a catalyst, to form dialkyl sulfite and the corresponding diol, (c) rearrangement of the dialkyl sulfite in the presence of a suitable catalyst to form the corresponding alkyl alkanesulfonate, (d) hydrolysis of the alkyl alkanesulfonate to give the desired alkanesulfonic acid, where some of the by-products formed in the various steps can be recirculated to the appropriate preceding steps or the diol formed in step (b) can be utilized as useful product.

The sulfur dioxide formed as by-product in step (c) can be recirculated to step (a) and the dialkyl ether formed in step (c) can, after hydrolysis to the corresponding alcohol, be recirculated to step (b). The alcohol formed in step (d) can likewise be recirculated to step (b).

The alkyl alkanesulfonate prepared in step (c) is preferably purified prior to hydrolysis to the corresponding alkanesulfonic acid (step (d)).

The alkanesulfonic acids preferably have alkyl radicals having from 1 to 3 carbon atoms, for example methyl, ethyl, n-propyl or i-propyl radicals, among which the methyl radical is very particularly preferred.

Consequently, the alcohol used (step (b)) is particulary preferably an alcohol having from 1 to 3 carbon atoms, e.g. methanol, ethanol, n-propanol or i-propanol, very particularly preferably methanol.

Dialkyl sulfites which are particularly preferably used (step (c)) are those having from 1 to 3 carbon atoms in their alkyl radicals, e.g. dimethyl sulfite, diethyl sulfite, di-n-propyl sulfite or di-i-propyl sulfite, very particularly preferably dimethyl sulfite.

The alkyl alkanesulfonates used (step (d)) are accordingly those having, particularly preferably, from 1 to 3 carbon atoms, very particularly preferably 1 carbon atom, in the alkyl radical. The alkyl radical and the radical in the ester group are preferably the same, so that methyl methanesulfonate is very particularly preferred.

The following example illustrates the invention.

EXAMPLE

Synthesis of Ethylene Sulfite from Ethylene Oxide and $SO_2$ 5 g of tetraethylammonium bromide dissolved in 500 g of ethylene sulfite were placed in a pressure reactor and heated to 170° C. Subsequently, 408 g of ethylene oxide and 622 g of $SO_2$ were slowly introduced as gases. The pressure was in the range from 4 to 8.5 bar. The reaction gave a crude product which comprised 96% (percent by area by GC) of ethylene sulfite.

Synthesis of Dimethyl Sulfite from Ethylene Sulfite

A stream of 100 g/h of ethylene sulfite and 0.44 g/h of methanesulfonic acid in liquid form (stream 1) was fed in above the 40 tray of a bubble tray column (60 trays, diameter=43 mm). At the bottom of the column, a temperature-regulated stream of 400 g/h of gaseous methanol was metered in. The major part of the methanol was recirculated from the second column and supplemented under temperature control with fresh methanol (60 g/h) (stream 2). The bottom of the column was heated to 192° C. and the bottoms were pumped out under level control (stream 3). The bottoms consisted predominantly of ethylene glycol together with a little oligoethylene glycol and catalyst. The vapor from the column was cooled to 75° C. by means of a reflux condenser and passed to a second column (packed column, diameter =43 mm, 2 m laboratory mesh packing, surface area=1000 $cm^2/cm^3$). This column was operated at a pressure of 800 mbar at the top. The bottom of the second column was heated to 105° C. The bottoms comprised the dimethyl sulfite and were discharged under level control (stream 4). The reflux ratio was set so that the temperature in the upper part of the column was 58° C.

Rearrangement of Dimethyl Sulfite to form Methyl Methanesulfonate 220 g of dimethyl sulfite and 18.5 g of tri-n-butylamine were placed in a 500 ml flask fitted with a reflux condenser and the mixture was heated under reflux to 130° C. on an oil bath. As the reaction proceeded, the temperature was increased to 170° C. over a period of 8 hours. The mixture became dark toward the end of the reaction. Work-up of the crude product by vacuum distillation (62° C., 6 mbar) gave 143 g (yield: 65%) of methyl methanesulfonate.

Preparation of Methanesulfonic Acid by Hydrolysis of Methyl Methanesulfonate A mixture of 80 g of methyl methanesulfonate and 130.9 g of $H_2O$ was heated to 98° C. while stirring vigorously. According to analysis by $^1$H-NMR spectroscopy, the ester was hydrolyzed completely after 45 minutes. The reaction mixture contained only methanesulfonic acid and methanol in addition to water. Part of the methanol liberated reacted during the course of the hydrolysis to form dimethyl ether which was given off in gaseous form.

We claim:
1. A process for preparing an alkanesulfonic acid, which comprises the following steps:
    (a) reacting an epoxide with sulfur dioxide to form alkylene sulfite,
    (b) countercurrently contacting the alkylene sulfite continuously with an alcohol to form dialkyl sulfite and a corresponding diol,
    (c) rearranging the dialkyl sulfite in the presence of one or more catalysts selected from the group consisting of an amine, an alkyl iodide, a quaternary ammonium salt, a quaternary phosphonium salt, a tertiary sulfonium salt, and an alkylating agent, to form a corresponding alkyl alkanesulfonate,
    (d) hydrolyzing the alkyl alkanesulfonate to give a alkanesulfonic acid.

2. The process as claimed in claim 1, wherein the alkyl alkanesulfonate is purified prior to hydrolysis.

3. The process as claimed in claim 1, wherein the alkanesulfonic acid has an alkyl radical with 1 to 3 carbon atoms.

4. The process as claimed in claim 3, wherein the alkyl radical is a methyl radical.

5. The process as claimed in claim 1, wherein the catalyst in step (c) is at a concentration of 0.01 to 20 mol %.

6. The process as claimed in claim 1, wherein said rearranging is at a temperature of 20 to 250° C.

7. The process as claimed in claim 2, wherein said purified is by distillation.

8. The process as claimed in claim 1, wherein 50 to 500 mol % water is added in step (d).

9. The process as claimed in claim 1, wherein said hydrolyzing is at a temperature of 80 to 180° C.

10. The process as claimed in claim 1, wherein said alcohol in step (b) is a monohydric alcohol.

11. The process as claimed in claim 1, wherein the alkylene sulfite in step (b) is of formula (I):

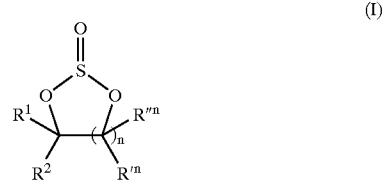

wherein n is from 1 to 6; $R^1$, $R^2$, $R'''$, and $R''''$ are independently hydrogen, an alkyl, or an aryl radical.

12. The process as claimed in claim 1, wherein step (b) further comprises a catalyst.

13. The process as claimed in claim 12, wherein the catalyst in step (b) is methanesulfonic acid.

14. The process as claimed in claim 12, wherein the catalyst in step (b) is at a concentration of 0.01 to 5 mol %.

15. The process as claimed in claim 1, wherein the epoxide in step (a) is of formula (II):

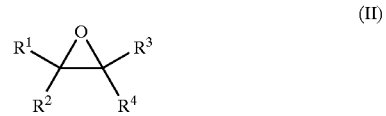

wherein $R^1$, $R^2$, $R^3$, and $R^4$ are independently hydrogen, alkyl, or aryl radicals.

16. The process as claimed in claim 1, wherein step (a) further comprises a catalyst.

17. The process as claimed in claim 16, wherein the catalyst in step (a) is a tetraethylammonium halide or a tetraethylammonium amine.

18. The process as claimed in claim 16, wherein the catalyst in step (a) is at a concentration of 0.01 to 10% by weight.

19. The process as claimed in claim 1, wherein sulfur dioxide formed as a by-product in step (c) can be recirculated to step (a).

20. The process as claimed in claim 1, wherein, after hydrolysis to the corresponding alcohol, a dialkyl ether formed in step (c) can be recirculated to step (b).

21. The process as claimed in claim 1, wherein an alcohol formed in step (d) can be recirculated to step (b).

* * * * *